United States Patent [19]
Grinnell et al.

[11] Patent Number: 6,071,514
[45] Date of Patent: Jun. 6, 2000

[54] METHODS FOR TREATING THROMBOTIC DISORDERS

[75] Inventors: Brian William Grinnell; Joseph Anthony Jakubowski, both of Indianapolis, Ind.

[73] Assignee: Eli Lilly and Company, Indianapolis, Ind.

[21] Appl. No.: 09/090,061

[22] Filed: Jun. 3, 1998

Related U.S. Application Data

[60] Provisional application No. 60/048,628, Jun. 5, 1997.

[51] Int. Cl.$^7$ ............................ A61K 34/48; A01N 37/36
[52] U.S. Cl. ........................................ 424/94.64; 574/165
[58] Field of Search .......................... 424/94.64; 514/165

[56] References Cited

U.S. PATENT DOCUMENTS

| | | | |
|---|---|---|---|
| 4,775,624 | 10/1988 | Bang et al. | 435/226 |
| 4,981,952 | 1/1991 | Yan | 530/384 |
| 4,992,373 | 2/1991 | Bang et al. | 435/69.6 |
| 5,350,578 | 9/1994 | Griffin et al. | 424/94.64 |
| 5,453,373 | 9/1995 | Gerlitz et al. | 514/2 |
| 5,516,650 | 5/1996 | Foster et al. | 435/68.1 |
| 5,618,843 | 4/1997 | Fisher et al. | 514/567 |

FOREIGN PATENT DOCUMENTS

| | | |
|---|---|---|
| 0 445 939 | 11/1991 | European Pat. Off. . |
| 5-271098 | 10/1993 | Japan . |
| 97/20043 | 6/1997 | WIPO . |

OTHER PUBLICATIONS

Popma et al., Adjuncts to Thrombolysis for Myocardial Reperfusion, Ann. Intern. Med., vol. 115, No. 1, pp. 34–44, Jul. 1991.

Gruber et al., Generation of Both Plasmin and Activated Protein C During Thrombolytic Therapy with Streptokinase. Blood, vol. 82, No. 10, Suppl. 1, p. 212a, Abstract No. 835, Nov. 1993.

Esmon, C. T., The Regulation of Natural Anticoagulant Pathways, Science, vol. 235, pp. 1348–1352, Mar. 1987.

Eisenberg, P.R., Role of New Anticoagulants as Adjunctive Therapy During Thrombolysis, Am. J. Cardiaol., vol. 67., No. 3, pp. A19–A24, Jan. 1991.

Verstraete, M., Advances in Thromolytic Therapy, Cardiovasc. Drugs Ther., vol. 6, No. 2, pp. 111–124, 1992.

Angelli, G., New Strategies for Enhancing the Speed and Rate of Coronary Reperfusion, Am. J. Cardiol., vol. 72, No. 9, pp. 51G–58G, Dec. 1993.

Runge et al., Inhibition of Platelets and Thrombin: Implications for Treatment of Coronary Artery Thrombosis, Z. Kardiol., vol. 82, Suppl. 2, pp. 83–88, 1993.

Grinnell, et al., "Trans–Activated Expression Of Fully Gamma–Carboxylated Recombinant Human Protein C, An Antithrombotic Factor", *Bio/Technology*, 5:1189–1192, Nov. 1987.

Remington, *The Science and Practice of Pharmacy*, Nineteenth Edition, vol. II, pp. 924–925, Mack Publishing Co. (1995).

Yasuda, et al., "Comparative Effects of Aspirin, a Synthetic Thrombin Inhibitor and a Monoclonal Antiplatelet Glycoprotein IIb/IIIa Antibody on Coronary Artery Reperfusion, Reocclusion and Bleeding With Recombinant Tissue–Type Plasminogen Activator in a Canine Perparation", *JACC*, vol. 16 No. 3, 714–722, Sep. 1990.

Clarke et al., "Combined Administration of Aspirin and a Specific Thrombin Inhibitor in Man", *Circulation/Clinical Investigation*, vol. 83, 1510–1518, 1991.

Jang et al., "Antiplatelets", *Current Science/ Coronary Artery Disease*, vol. 3, No. 11, 1030–1036, Nov. 1992.

Zoldhelyi, et al., "Antithrombins as conjuctive therapy in arterial thrombolysis", *Current Science/Coronary Artery Disease*, vol. 3, No. 11, 1003–1009, Nov. 1992.

Heiden, et al., "Impairment by Heparin of Primary Haemostasis and Platelet [$^{14}$C]5–Hydroxytryptamine Release", *British Journal of Haematology*, 36:427–436, 1977.

*Primary Examiner*—Jon P. Weber
*Attorney, Agent, or Firm*—Lynn D. Apelgren; Brian P. Barrett; Steven P. Caltrider

[57] ABSTRACT

The present invention provides a method of treatment for patients with a variety of thrombotic disorders including, but not limited to, stroke, venous thrombosis, myocardial infarction, unstable angina, abrupt closure following angioplasty or stent placement, and thrombosis as a result of peripheral vascular surgery. Said treatment is a combination therapy with human aPC and antiplatelet agents including, but not limited to, aspirin (ASA), clopidogrel, ReoPro® (abciximab), dipyridamole, ticlopidine and IIb/IIIa receptor antagonists. The synergy will result in the ability to reduce the dosages of the agents used in the combination therapy.

20 Claims, No Drawings

METHODS FOR TREATING THROMBOTIC DISORDERS

This application claims the benefit of U.S. Provisional Application Ser. No. 60/048,628, filed Jun. 5, 1997.

FIELD OF THE INVENTION

This invention relates to medical science particularly the treatment of thrombotic disorders with activated human protein C in combination with antiplatelet agents.

BACKGROUND OF THE INVENTION

Protein C is a serine protease and naturally occurring anticoagulant that plays a role in the regulation of hemostasis by inactivating Factors Va and VIIIa in the coagulation cascade. Human protein C circulates as a 2-chain zymogen which is activated in vivo by thrombin and thrombomodulin on phospholipid surfaces resulting in activated protein C (aPC).

Blood coagulation is a highly complex process regulated by the balance between pro-coagulant and anticoagulant mechanisms. This balance determines a condition of either normal hemostasis or abnormal pathological thrombus formation leading to events such as stroke, myocardial infarction and venous thrombosis. Two major factors control this balance, the generation of fibrin and the activation and subsequent aggregation of platelets. A critical factor controlling both processes is the generation of the enzyme thrombin, which occurs following activation of the clotting cascade. Thrombin is a pro-coagulant enzyme that aggregates platelets and converts circulating fibrinogen to insoluble fibrin, resulting in the formation of a blood clot. Thrombin also functions as a potent anticoagulant since it activates protein C zymogen to activated protein C, which in turn inhibits the generation of thrombin. Thus, through the feedback regulation of thrombin generation, aPC functions as perhaps the most important down-regulator of blood coagulation resulting in protection against thrombosis.

The critical role of protein C in controlling hemostasis is exemplified by the increased rate of thrombosis in heterozygous deficiency, protein C resistance (e.g., due to the common Factor V Leiden mutation) and the fatal outcome of untreated homozygous protein C deficiency. Human activated protein C, both plasma-derived and recombinant, have been shown to be effective and safe antithrombotic agents in a variety of animal models of both venous and arterial thrombosis.

In current clinical practice, platelet inhibition, e.g., using aspirin (ASA), is well documented for efficacy in both prevention and treatment of thrombotic disease. Moreover, in conditions such as myocardial infarction and stroke, platelet inhibition has become the standard of care. However, the use of antiplatelet agents such as ASA increases the risk of bleeding, which limits the dose of the agent and duration of treatment. To block the effect of thrombin in fibrin formation, heparin remains the standard anticoagulant in the acute care setting. However, heparin has a narrow therapeutic index and is associated with significant bleeding risk especially in combination with antiplatelet agents.

Combination therapy with aspirin and a synthetic thrombin inhibitor, tissue plasminogen activator, or a monoclonal antiplatelet glycoprotein IIb/IIIa antibody has been studied in a canine coronary artery thrombosis model [Yasuda, et al., J Am Coll Cardiol., 16:714–22 (1990)]. Aspirin in combination with these agents prolonged the bleeding time and did not prevent reocclusion of the coronary artery. In addition, combination therapy has been proposed for aPC with thrombolytic agents such as tissue plasminogen activator, urokinase, or streptokinase [Griffin, et al., U.S. Pat. No. 5,350,578]. However, these combinations have not proved successful. Thus, there remains the need to identify an effective therapy for treating thrombotic disorders.

The present invention is the first to describe the combination of aPC with antiplatelet agents in the treatment of thrombosis. Accordingly, the present invention provides the use of aPC in combination with antiplatelet agents for the treatment of thrombotic disorders. This combination therapy results in enhanced efficacy in a variety of thrombotic disorders including, but not limited to, stroke, myocardial infarction, unstable angina, abrupt closure following angioplasty or stent placement, and thrombosis as a result of peripheral vascular surgery. Furthermore, the combination of aPC and antiplatelet agents results in a synergy that will allow the reduction of the dosages of both aPC and the antiplatelet agents. The reduction of the dosages of the agents in combination therapy in turn results in reduced side effects such as increased bleeding liability often observed in combination anticoagulant/antiplatelet therapy.

SUMMARY OF THE INVENTION

The present invention provides a method of treating a thrombotic disorder in a patient in need thereof, which comprises administering to said patient a pharmaceutically effective amount of activated protein C in combination with an antiplatelet agent. Additionally, the invention provides a method of treating a thrombotic disorder in a patient in need thereof, which comprises administering to said patient a pharmaceutically effective amount of an antiplatelet agent and activated protein C such that an activated protein C plasma level of 10 ng/ml to less than 100 ng/ml is achieved.

DETAILED DESCRIPTION OF THE INVENTION

For purposes of the present invention, as disclosed and claimed herein, the following terms are as defined below.

aPC or activated protein C whether recombinant or plasma derived. aPC includes and is preferably human protein C although aPC may also include other species or derivatives having protein C proteolytic, amidolytic, esterolytic, and biological (anticoagulant or pro-fibrinolytic) activities. Examples of protein C derivatives are described by Gerlitz, et al., U.S. Pat. No. 5,453,373, and Foster, et al., U.S. Pat. No. 5,516,650, the entire teachings of which are hereby included by reference.

APTT—activated partial thromboplastin time.

HPC—human protein C zymogen.

r-hPC—recombinant human protein C zymogen, produced in prokaryotic cells, eukaryotic cells or transgenic animals.

r-aPC—recombinant human activated protein C produced by activating r-hPC in vitro or by direct secretion of the activated form of protein C from procaryotic cells, eukaryotic cells, or transgenic animals [Cottingham, WO97/20043] including, for example, secretion from human kidney 293 cells as a zymogen then purified and activated by techniques well known to the skilled artisan demonstrated in Yan, U.S. Pat. No. 4,981,952, and, the entire teachings of which are herein incorporated by reference.

Zymogen—refers to secreted, inactive forms, whether one chain or two chains of protein C.

Antiplatelet agent—one or more agents alone or in combination which reduces the ability of platelets to aggregate. Agents understood and appreciated in the art include those cited in, for example, Remington, *The Science and Practice of Pharmacy*, Nineteenth Edition, Vol II, Pages 924–25, Mack Publishing Co., herein incorporated by reference. Such agents include but are not limited to aspirin (ASA),clopidogrel, ReoPro® (abciximab), dipyridamole, ticlopidine and glycoprotein IIb/IIIa antagonists.

Treating—describes the management and care of a patient for the purpose of combating the disease, condition, or disorder and includes the administration of a compound of the present invention to prevent the onset of the symptoms or complications, alleviating the symptoms or complications, or eliminating the disease, condition, or disorder.

Continuous infusion—continuing substantially uninterrupted the introduction of a solution into a vein for a specified period of time.

Bolus injection—the injection of a drug in a defined quantity (called a bolus) over a period of time up to about 120 minutes.

Pharmaceutically effective amount—represents an amount of a compound of the invention that is capable of inhibiting a thrombotic disorder in mammals. The particular dose of the compound administered according to this invention will, of course, be determined by the attending physician evaluating the particular circumstances surrounding the case, including the compound administered, the particular condition being treated, and similar considerations.

Thrombotic disorder—a disorder relating to, or affected with the formation or presence of a blood clot within a blood vessel. Thrombotic disorders include, but are not limited to, stroke, myocardial infarction, unstable angina, abrupt closure following angioplasty or stent placement, and thrombosis as a result of peripheral vascular surgery.

The present invention preferably relates to the treatment of thrombotic disorders with activated protein C in combination with an antiplatelet agent. The aPC used in such combination can be formulated according to known methods to prepare pharmaceutically useful compositions. The aPC will be administered parenterally to ensure its delivery into the bloodstream in an effective form by injecting the appropriate dose as continuous infusion for about 24 hours to about 144 hours.

In conjunction with treatment with an antiplatelet agent, the amount of aPC administered will be from about 4 mg/70 Kg/24 hours to 160 mg/70 kg/24 hours or an equivalent designations of 0.1 mg/m$^2$ to 4 mg/m$^2$ or 2 $\mu$g/kg/hr to 96 $\mu$g/kg/hr. More preferably the amount of aPC administered will be about 4 mg/70 Kg/24 hours to 120 mg/70 Kg/24 hours or an equivalent designations of 0.1 mg/m$^2$ to 3 mg/m$^2$ or 2.4 $\mu$g/kg/hr to 72 $\mu$g/kg/hr. While more preferably the amount of aPC administered will be about 4 mg/70 Kg/24 hours to 80 mg/70 kg/24 hours or an equivalent designation of 0.1 mg/m$^2$ to 2 mg/m$^2$ or 2.4 $\mu$g/kg/hr to 48 $\mu$g/kg/hr. Even more preferably the amount of aPC administered will be about 4 mg/70 Kg/24 hours to 60 mg/70 kg/24 hours or an equivalent designations of 0.1 mg/m$^2$ to 1.5 mg/m$^2$ or 2.4 $\mu$g/kg/hr to 36 $\mu$g/kg/hr. Yet even more preferably the amount of aPC administered will be about 10 mg/70 Kg/24 hours to 50 mg/70 kg/24 hours or an equivalent designations of 0.25 mg/m$^2$ to 1.25 mg/m$^2$ or 6 $\mu$g/kg/hr to 30 $\mu$g/kg/hr. Still even more preferably the amount of aPC administered will be about 20 mg/70 kg/24 hours to 40 mg/70 kg/24 hours or an equivalent designations of 0.5 mg/m$^2$ to 1.0 mg/m$^2$ or 12 $\mu$g/kg/hr to 24 $\mu$g/kg/hr. The most preferable amount of aPC administered will be about 40 mg/70 kg/24 hours or an equivalent designation of 1.0 mg/m$^2$ or 24 $\mu$g/kg/hr. The appropriate dose of aPC administered with an antiplatelet therapeutic will result in either an improved efficacy or reduction in dose of either agent or both.

The plasma ranges obtained from the amount of aPC administered will be 2 ng/ml to less than 100 ng/ml. The preferred plasma ranges are from about 20 ng/ml to 80 ng/ml. Most preferably plasma ranges are from about 30 ng/ml to about 60 ng/ml and still more preferably about 50 ng/ml.

Alternatively, the aPC will be administered by injecting one third of the appropriate dose per hour as a bolus injection followed by the remaining two thirds of the hourly dose as continuous infusion for one hour followed by continuous infusion of the appropriate dose for twenty-three hours which results in the appropriate dose administered over 24 hours.

The phrase "in combination with" refers to the administration of antiplatelet agents with aPC either simultaneously, sequentially or a combination thereof. The administration of platelet inhibitiors in combination with aPC will result in enhanced efficacy in a variety of thrombotic disorders including, but not limited to, stroke, venous thrombosis, myocardial infarction, unstable angina, abrupt closure following angioplasty or stent placement, and thrombosis as a result of peripheral vascular surgery. The synergy also will result in ability to reduce the dosages of agents in combination therapy resulting in reduced side effects such as increases in bleeding liability often observed in combination anticoagulant/antiplatelet therapy.

The antiplatelet agent utilized and the appropriate dose level is understood and appreciated in the art. A skilled artisan recognizes the appropriate dose level to use for each antiplatelet agent to achieve a pharmaceutically effective amount for treating thrombotic disorders. Antiplatelet agents suitable for use under the present invention include, but are not limited to, clinically recognized and commercially available agents such as aspirin (ASA),clopidogrel, ReoPro® (abciximab), dipyridamole, ticlopidine and glycoprotein IIb/IIIa antagonists. The amount of the antiplatelet agent aspirin (ASA) administered in conjunction with aPC will be about 10 mg to 1000 mg, given once daily. The amount of the antiplatelet agent ticlopidine administered in conjunction with aPC will be about 50 mg to 1250 mg, given two times daily (B.I.D.). The amount of the antiplatelet agent dipyridamole administered in conjunction with aPC will be about 15 mg to 500 mg, given four times daily. The amount of the antiplatelet agent clopidogrel administered in conjunction with aPC will be about 40 mg to 1000 mg, given once a day. The amount of the antiplatelet agent ReoPro® (abciximab) administered in conjunction with aPC will be about 0.025 $\mu$g/kg/min to 1 $\mu$g/kg/min given as an infusion for twelve hours. Alternatively, ReoPro® can be administered in conjunction with aPC as a bolus injection at about 0.05 mg/kg to 1.0 mg/kg. In addition, ReoPro® can be administered in conjunction with aPC as a bolus injection followed by an infusion for twelve hours. The amount of the IIb/IIIa antagonist utilized in combination with aPC will be about 0.1 mg/kg to about 100 mg/kg depending on the specific agent employed [see for example, Fisher, et al., U.S. Pat. No. 5,618,843, the entire teaching of which is herein incorporated by reference]. One skilled in the art will be able to determine the appropriate dose level to use to achieve a pharmaceutically effective amount.

The aPC combined with the antiplatelet agents improves the antithrombotic effect of an antiplatelet agent alone. Thus, this combination therapy may reduce the therapeutic doses of aPC as well as reduce doses of antiplatelet agents required for therapeutic treatment of thrombosis, thereby avoiding the complications such as bleeding tendency, toxicity and general side effects of high doses of antiplatelet agents.

Preparation 1

Preparation of Human Protein C

Recombinant human protein C (r-hPC) was produced in Human Kidney 293 cells by techniques well known to the skilled artisan such as those set forth in Yan, U.S. Pat. No. 4,981,952, the entire teaching of which is herein incorporated by reference. The gene encoding human protein C is disclosed and claimed in Bang, et al., U.S. Pat. No. 4,775,624, the entire teaching of which is incorporated herein by reference. The plasmid used to express human protein C in 293 cells was plasmid pLPC which is disclosed in Bang, et al., U.S. Pat. No. 4,992,373, the entire teaching of which is incorporated herein by reference. The construction of plasmid pLPC is also described in European Patent Publication No. 0 445 939, and in Grinnell, et al., 1987, *Bio/Technology* 5:1189–1192, the teachings of which are also incorporated herein by reference. Briefly, the plasmid was transfected into 293 cells, then stable transformants were identified, subcultured and grown in serum-free media. After fermentation, cell-free medium was obtained by microfiltration.

The human protein C was separated from the culture fluid by an adaptation of the techniques of Yan, U.S. Pat. No. 4,981,952, the entire teaching of which is herein incorporated by reference. The clarified medium was made 4 mM in EDTA before it was absorbed to an anion exchange resin (Fast-Flow Q, Pharmacia). After washing with 4 column volumes of 20 mM Tris, 200 mM NaCl, pH 7.4 and 2 column volumes of 20 mM Tris, 150 mM NaCl, pH 7.4, the bound recombinant human protein C zymogen was eluted with 20 mM Tris, 150 mM NaCl, 10 mM $CaCl_2$, pH 7.4. The eluted protein was greater than 95% pure after elution as judged by SDS-polyacrylamide gel electrophoresis.

Further purification of the protein was accomplished by making the protein 3 M in NaCl followed by adsorption to a hydrophobic interaction resin (Toyopearl Phenyl 650 M, TosoHaas) equilibrated in 20 mM Tris, 3 M NaCl, 10 mM $CaCl_2$, pH 7.4. After washing with 2 column volumes of equilibration buffer without $CaCl_2$, the recombinant human protein C was eluted with 20 mM Tris, pH 7.4.

The eluted protein was prepared for activation by removal of residual calcium. The recombinant human protein C was passed over a metal affinity column (Chelex-100, Bio-Rad) to remove calcium and again bound to an anion exchanger (Fast Flow Q, Pharmacia). Both of these columns were arranged in series and equilibrated in 20 mM Tris, 150 mM NaCl, 5 mM EDTA, pH 6.5. Following loading of the protein, the Chelex-100 column was washed with one column volume of the same buffer before disconnecting it from the series. The anion exchange column was washed with 3 column volumes of equilibration buffer before eluting the protein with 0.4 M NaCl, 20 mM Tris-acetate, pH 6.5. Protein concentrations of recombinant human protein C and recombinant activated protein C solutions were measured by UV 280 nm extinction $E^{0.1\%}$=1.81 or 1.85, respectively.

Preparation 2

Activation of Recombinant Human Protein C

Bovine thrombin was coupled to Activated CH-Sepharose 4B (Pharmacia) in the presence of 50 mM HEPES, pH 7.5 at 4° C. The coupling reaction was done on resin already packed into a column using approximately 5000 units thrombin/ml resin. The thrombin solution was circulated through the column for approximately 3 hours before adding MEA to a concentration of 0.6 ml/l of circulating solution. The MEA-containing solution was circulated for an additional 10–12 hours to assure complete blockage of the unreacted amines on the resin. Following blocking, the thrombin-coupled resin was washed with 10 column volumes of 1 M NaCl, 20 mM Tris, pH 6.5 to remove all non-specifically bound protein, and was used in activation reactions after equilibrating in activation buffer.

Purified r-hPC was made 5 mM in EDTA (to chelate any residual calcium) and diluted to a concentration of 2 mg/ml with 20 mM Tris, pH 7.4 or 20 mM Tris-acetate, pH 6.5. This material was passed through a thrombin column equilibrated at 37° C. with 50 mM NaCl and either 20 mM Tris pH 7.4 or 20 mM Tris-acetate pH 6.5. The flow rate was adjusted to allow for approximately 20 min. of contact time between the r-hPC and thrombin resin. The effluent was collected and immediately assayed for amidolytic activity. If the material did not have a specific activity (amidolytic) comparable to an established standard of aPC, it was recycled over the thrombin column to activate the r-hPC to completion. This was followed by 1:1 dilution of the material with 20 mM buffer as above, with a pH of anywhere between 7.4 or 6.0 (lower pH being preferable to prevent autodegradation) to keep the aPC at lower concentrations while it awaited the next processing step.

Removal of leached thrombin from the aPC material was accomplished by binding the aPC to an anion exchange resin (Fast Flow Q, Pharmacia) equilibrated in activation buffer (either 20 mM Tris, pH 7.4 or preferably 20 mM Tris-acetate, pH 6.5) with 150 mM NaCl. Thrombin passes through the column and elutes during a 2–6 column volume wash with 20 mM equilibration buffer. Bound aPC is eluted with a step gradient using 0.4 M NaCl in either 5 mM Tris-acetate, pH 6.5 or 20 mM Tris, pH 7.4. Higher volume washes of the column facilitated more complete removal of the dodecapeptide. The material eluted from this column was stored either in a frozen solution (−20° C.) or as a lyophilized powder.

The amidolytic activity (AU) of aPC was determined by release of p-nitroanaline from the synthetic substrate H-D-Phe-Pip-Arg-p-nitroanilide (S-2238) purchased from Kabi Vitrum using a Beckman DU-7400 diode array spectrophotometer. One unit of activated protein C was defined as the amount of enzyme required for the release of 1 $\mu$mol of p-nitroaniline in 1 min. at 250° C., pH 7.4, using an extinction coefficient for p-nitroaniline at 405 nm of 9620 $M^{-1}cm^{-1}$.

The anticoagulant activity of activated protein C was determined by measuring the prolongation of the clotting time in the activated partial thromboplastin time (APTT) clotting assay. A standard curve was prepared in dilution buffer (1 mg/ml radioimmunoassay grade BSA, 20 mM Tris, pH 7.4, 150 mM NaCl, 0.02% $NaN_3$) ranging in protein C concentration from 125–1000 ng/ml, while samples were prepared at several dilutions in this concentration range. To each sample cuvette, 50 $\mu$l of cold horse plasma and 50 $\mu$l of reconstituted activated partial thromboplastin time reagent (APTT Reagent, Sigma) were added and incubated at 37° C. for 5 min. After incubation, 50 $\mu$l of the appropriate samples or standards were added to each cuvette. Dilution buffer was used in place of sample or standard to determine basal clotting time. The timer of the fibrometer (CoA Screener Hemostasis Analyzer, American Labor) was started upon the addition of 50 μl 370° C. 30 mM CaCl$_2$ to each sample or standard. Activated protein C concentration in samples are calculated from the linear regression equation of the standard curve. Clotting times reported here are the average of a minimum of three replicates, including standard curve samples.

Preparation 3

Formulation of Activated Protein C

A stable lyophilized formulation of activated protein C was prepared by a process which comprises lyophilizing a solution comprising about 2.5 mg/mL activated protein C, about 15 mg/mL sucrose, about 20 mg/mL NaCl, and a sodium citrate buffer having a pH greater than 5.5 but less than 6.5. Additionally, the stable lyophilized formulation of activated protein C comprises lyophilizing a solution comprising about 5 mg/mL activated protein C, about 30 mg/mL sucrose, about 38 mg/mL NaCl, and a citrate buffer having a pH greater than 5.5 but less than 6.5.

The ratio of aPC:salt:bulking agent (w:w:w) is an important factor in a formulation suitable for the freeze drying process. The ratio varies depending on the concentration of aPC, salt selection and concentration and bulking agent selection and concentration. Particularly, a ratio of about 1 part activated protein C to about 7.6 parts salt to about 6 parts bulking agent is preferred.

A unit dosage formulation of activated protein C suitable for administration by continuous infusion was prepared by mixing activated protein C, NaCl, sucrose, and sodium citrate buffer. After mixing, 4 mL of the solution was transferred to a unit dosage receptacle and lyophilized. The unit dosage receptacle containing about 5 mg to about 20 mg of activated protein C, suitable for administering a dosage of about 0.01 mg/kg/hr to about 0.05 mg/kg/hr to patients in need thereof, was sealed and stored until use.

EXAMPLE 1

Guinea Pig AV shunt model of thrombosis

Because platelet inhibition has proven clinical efficacy and aPC plays a critical role in controlling hemostasis, the possible synergy between aPC and ASA was examined in the Guinea Pig arterial/venous (AV) shunt thrombosis model. In this model of thrombosis, aPC has been shown to be an effective antithrombotic agent, causing dose-dependent inhibition of thrombus formation.

To examine the effect of aPC and aspirin, Guinea pigs (approximately 500 g) were anesthetized with 20 mg/kg Rompun and 125 mg/kg Ketaset, and a shunt was inserted connecting the right carotid artery and the left jugular vein. The shunt contained a cotton thread which stimulated thrombus formation. aPC was administered to inhibit thrombus formation with a bolus plus infusion dosing regimen (0.5 mg/kg bolus plus 3 mg/kg/hr). Additionally, whole blood aPTT was performed before and during the dosing regimen and circulating aPC plasma levels were measured by immunocapture amidolytic assay. Aspirin was administered at 10 mg/kg, intravenously, and in studies with heparin, a dose of 30 units/kg bolus followed by an infusion of 40 units/kg/hr was used. Bolus dosing was performed via cannulation of the left jugular vein and blood sampling was performed via cannulation of the right jugular vein. Blood samples were drawn at consecutive time points into 3.8% Na$_3$ citrate containing 300 mM Benzamidine HCl (9 volumes blood to 1 volume citrate/benzamidine solution). Blood volume was replaced in the animal with saline after each draw. Plasma was separated by centrifugation and frozen at −20° C. Plasma concentration of aPC was determined by an immunocapture amidolytic assay.

To examine potential antithrombotic synergism between aPC and the anti-platelet agent ASA, the dose of ASA was chosen to give near completed inhibition of platelet cyclo-oxygenase, as measured by inhibition of thromboxane B2 release. As shown in Table 1, a dose of 10 mg/kg ASA effectively inhibited platelet cyclo-oxygenase, however it had no significant effect on thrombus weight. Using this dose of ASA, which caused no effect on thrombus weight, experiments in conjunction with aPC were performed. For comparative purposes, heparin, the standard clinical anticoagulant, was also compared. As shown in Table 2, the dose of aPC and heparin were chosen to each give approximately the same antithrombotic effect in the model (45.9 and 43.3% inhibition, respectively). The combination of ASA and aPC resulted in a significantly greater inhibition of thrombus formation than was observed with aPC alone (p=0.01). In contrast, the combination of the anticoagulant heparin with ASA showed no significantly greater effect than that observed with heparin alone. These data demonstrate a synergy between anti-platelet agents and aPC, and suggest that: (a) patients on either ASA or other antiplatelet agents therapy will achieve increased efficacy by combination therapy with aPC, and (b) therapeutic doses of aPC may be reduced in presence of anti-platelet therapy.

TABLE 1

The effect of ASA on platelet Thromboxane B2 release and thrombus weight in the Guinea Pig AV-Shunt model. The data shows that despite near maximal inhibition of Thromboxane B2 release, ASA had no effect on thrombus weight.

| Treatment | Thromboxane B2 Release | Thrombus Weight |
|---|---|---|
| Control (PBS) | 638 ng/ml | 38.3 ± 1.1 mg (n = 10) |
| ASA (10 mg/Kg) | 10 ng/ml | 36.4 ± 1.3 mg (n = 8) |

TABLE 2

Antithrombotic synergism between aPC, but not heparin, and ASA.

| Treatment | Thrombus Weight* (minus ASA) | Thrombus Weight* (plus ASA) |
|---|---|---|
| Control | 100 ± 3 | 95 ± 3 |
| aPC | 46 ± 5 | 27 ± 5(p = 0.01) |
| Heparin | 43 ± 5 | 39 ± 6 |

*% of control

EXAMPLE 2

The Effect of aPC and a IIb/IIIa antagonist in the Guinea Pig AV Shunt Model of Thrombosis To examine the effect of combination therapy of aPC and a representative synthetic IIb/IIIa receptor antagonist, the guinea pig AV shunt model of thrombosis as described in Example 1, was utilized. 2-([6-carboxy-n-hexyl] carboxamidyl)-5-amidino benzofuran trifluoroacetate prepared as described in Fisher, et al., U.S. Pat. No. 5,618,843 was used. The combination of aPC and the IIb/IIIa antagonist resulted in a significantly greater inhibition of thrombus formation than was observed with aPC alone (Table 3).

These data demonstrate a synergy between aPC and a synthetic IIb/IIIa antagonist.

TABLE 3

Antithrombotic synergism between aPC and a IIb/IIIa antagonist

| Treatment | Thrombus Weight* (minus IIb/IIIa antagonist) | Thrombus Weight* (plus IIb/IIIa antagonist |
|---|---|---|
| Control | 100 ± 3 | 82 ± 3 |
| aPC | 46 ± 5 | 9 ± 1 |

*% of control

EXAMPLE 3

The Effect of aPC and abciximab in the Treatment of Thrombotic Disorders

Abiciximab (ReoPro®) is an agent which inhibits platelet aggregation by binding to IIb/IIIa receptors on the platelet cell surface. Combination therapy with aPC and abciximab is effective in inhibiting thrombosis by down-regulating the blood coagulation process and inhibiting platelet aggregation. Abciximab is administered as a bolus injection at about 0.05 mg/kg to about 1.0 mg/kg followed by a continuous infusion of about 0.025 ug/kg/min to about 1 ug/kg/min for 12 hours. aPC is administered as a bolus injection followed by a continuous infusion or as a continuous infusion of about 2 µg/kg/hr to about 96 µg/kg/hr for about 24 to about 144 hours.

This combination therapy results in a synergy that is safer and more efficacious and reduces the dosages of both aPC and abciximab necessary to treat thrombotic disorders.

We claim:

1. A method of treating a thrombotic disorder in a patient in need thereof, which comprises, administering to said patient a pharmaceutically effective amount of a combination of activated protein C and an antiplatelet agent.

2. The method according to claim 1, wherein said thrombotic disorder is selected from the group consisting of acute thrombotic stroke, venous thrombosis, myocardial infarction, unstable angina, abrupt closure following angioplasty or stent placement, and thrombosis as a result of peripheral vascular surgery.

3. The method according to claim 2, wherein the amount of activated protein C administered is about 2 µg/kg/hr to about 96 µg/kg/hr.

4. The method of claim 3, wherein the activated protein C is administered by continuous infusion for about 24 to about 144 hours.

5. The method according to claim 3, wherein said antiplatelet agent is selected from the group consisting of aspirin (ASA), clopidogrel, abciximab, dipyridamole, ticlopidine and glycoprotein, IIb/IIIa antagonists.

6. A method according to claim 5, wherein said antiplatelet agent is aspirin (ASA).

7. A method according to claim 5, wherein said antiplatelet agent is ticlopidine.

8. A method according to claim 5, wherein said antiplatelet agent is clopidogrel.

9. A method according to claim 5, wherein said antiplatelet agent is abciximab.

10. A method according to claim 5, wherein said antiplatelet agent is dipyridamole.

11. A method according to claim 5, wherein said antiplatelet agent is a glycoprotein IIb/IIIa receptor antagonist.

12. A method of treating a thrombotic disorder in a patient in need thereof, which comprises administering to said patient a pharmaceutically effective amount of an antiplatelet agent and activated protein C such that an activated protein C plasma level of 10 ng/ml to less than 100 ng/ml is achieved.

13. The method of claim 12, wherein said thrombotic disorder is selected from the group consisting of acute thrombotic stroke, venous thrombosis, myocardial infarction, unstable angina, abrupt closure following angioplasty or stent placement, and thrombosis as a result of peripheral vascular surgery.

14. The method of claim 12 wherein the activated protein C is administered by continuous infusion for about 24 to about 144 hours.

15. The method of claim 14 wherein the activated protein C is administered first as a bolus then as a continuous infusion.

16. A method according to claim 5, wherein said antiplatelet agent is aspirin (ASA) and clopidogrel.

17. A method according to claim 5, wherein said antiplatelet agent is aspirin (ASA) and ticlopidine.

18. A method according to claim 5, wherein said antiplatelet agent is aspirin (ASA) and dipyridamole.

19. A method according to claim 5, wherein said antiplatelet agent is aspirin (ASA) and abciximab.

20. A method according to claim 5, wherein said antiplatelet agent is aspirin (ASA) and a glycoprotein IIb/IIIa receptor antagonists.

* * * * *